(12) United States Patent
Chen et al.

(10) Patent No.: US 9,718,765 B1
(45) Date of Patent: Aug. 1, 2017

(54) PROCESS FOR PREPARATION OF OPTICALLY PURE N-SUBSTITUTED-3-METHOXYPROPIONIC ACID DERIVATIVES

(71) Applicant: SCI Pharmtech, Inc., Taoyuan (TW)

(72) Inventors: Bo-Fong Chen, Taoyuan (TW); Yen-Chi Su, Taoyuan (TW); Yen-Wei Li, Taoyuan (TW); Feng-Hsu Li, Taoyuan (TW); Chen-Wei Huang, Taoyuan (TW)

(73) Assignee: SCI Pharmtech, Inc., Taoyuan (TW)

( * ) Notice: Subject to any disclaimer, the term of this patent is extended or adjusted under 35 U.S.C. 154(b) by 0 days.

(21) Appl. No.: 15/188,559

(22) Filed: Jun. 21, 2016

(51) Int. Cl.
*C07C 269/06* (2006.01)
*C07C 269/04* (2006.01)
*C07C 231/12* (2006.01)
*C07C 231/08* (2006.01)

(52) U.S. Cl.
CPC .......... *C07C 269/06* (2013.01); *C07C 231/08* (2013.01); *C07C 231/12* (2013.01); *C07C 269/04* (2013.01)

(58) Field of Classification Search
None
See application file for complete search history.

(56) References Cited

U.S. PATENT DOCUMENTS

| 6,048,899 | A | 4/2000 | Kohn et al. |
| 8,809,585 | B2 | 8/2014 | Riedner et al. |
| 2014/0018577 | A1* | 1/2014 | Merschaert ............. C12P 13/06 564/136 |

FOREIGN PATENT DOCUMENTS

WO WO 2012/051551 A1 4/2012

* cited by examiner

*Primary Examiner* — Clinton Brooks
(74) *Attorney, Agent, or Firm* — Leydig, Voit & Mayer, Ltd.

(57) ABSTRACT

A method of producing optically pure N-substituted-3-methoxy propionic acid is provided, which includes the steps of:

reacting N-substituted-3-methoxy propionic acid represented by formula (III):

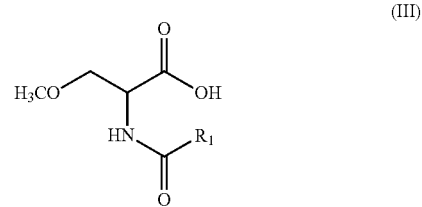

(III)

with a chiral amine in a solvent to obtain a diastereomeric salt represented by formula (IV):

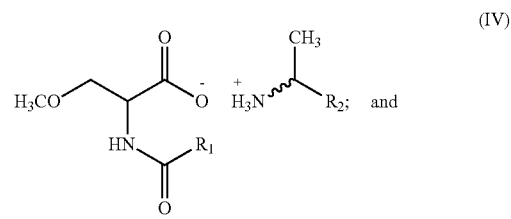

(IV)

subjecting the diastereomeric salt to a sequential washing process to obtain the optically pure N-substituted-3-methoxy propionic acid represented by one of formulae (Ia) and (Ib):

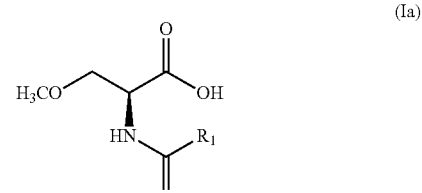

(Ia)

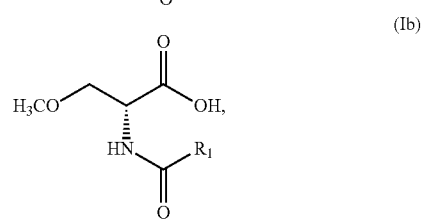

(Ib)

wherein $R_1$ is selected from the group consisting of $C_{1-5}$ alkyl, $C_{1-6}$ alkoxy and $C_{6-10}$ aryloxy group, and $R_2$ is selected from the group consisting of $C_{2-5}$ alkyl, $C_{6-8}$ cycloalkyl and $C_{6-10}$ aryl.

20 Claims, No Drawings

PROCESS FOR PREPARATION OF OPTICALLY PURE N-SUBSTITUTED-3-METHOXYPROPIONIC ACID DERIVATIVES

TECHNICAL FIELD

The present disclosure relates to an improved process by chiral resolution affording optical pure N-substituted-3-methoxypropionic acid with a high enantiomeric excess value and purity.

BACKGROUND

Amino acids are important chiral sources and act as skeletons in drug discovery. Besides amino and carboxyl groups, some of them bear different functional groups for further modification. Methylation on the terminal hydroxyl group of serine or threonine is an example, and there are several potential agents in the clinic or being approved.

Lacosamide is a typical example of an anti-convulsant agent with a O-methyl-serine skeleton. The same skeleton was also observed in Oprozomib as an anti-cancer drug in the phase II clinical trial. However, the methylation on the terminal hydroxyl group of serine is not very easy. In U.S. Pat. No. 6,048,899, O-methylation was carried out by using silver (I) oxide and iodomethane. However, this process is impractical due to high cost and resulted in around 15% racemisation.

In U.S. Pat. No. 8,809,585, the method described that N-Boc-D-Serine was methylated in the presence of sodium hydroxide in a two-phase system. Chirality increased to 98.1%, but not good enough. On the other hand, HPLC purity was only 96.3%. Although it is claimed in the patent that the chirality was 100% when base changed from sodium hydroxide to n-butyllithium, the purity of product was only 90%. Similar results are also observed in other patents such as WO2012/51551 in which the purity of N-Boc-D-Serine was only higher than 95%.

SUMMARY

In light of above-mentioned problems in the prior art, the present disclosure relates to an improved process for the preparation of optically pure N-substituted-3-methoxypropionic acid represented by formula (I). In the present disclosure, the term "optically pure" means that an enatiomer excess (e.e.) value is higher than 99%. The term "high purity" means that purity determined by HPLC is higher than 99%.

In an embodiment of the present disclosure, a process for preparing optically pure N-substituted-3-methoxypropionic acid represented by formula (I) may comprise reacting a chiral resolution of N-substituted-3-methoxypropionic acid with a suitable amine to form a diastereomeric salt. The specific configuration could be purified via recrystallization in an appropriate solvent system. Finally, the salt can be liberated to a free form in a basic solution.

In another embodiment of the present disclosure, N-substituted-3-methoxypropionic acid represented by formula (I) could serve as an intermediate compound for the synthesis of lacosamide or APIs. The preparation of the N-substituted-3-methoxypropionic acid represented by formula (I) comprises the following steps of:

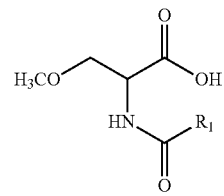

(a) N-acylating D- or L-serine;
(b) methylating N-acylated serine; and
(c) resoluting N-substituted-3-methoxypropionic with amine.

In another embodiment of the present disclosure, the optically pure N-substituted-3-methoxy propionic acid is represented by the following formula:

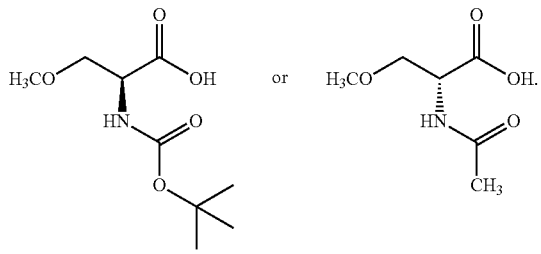

DETAILED DESCRIPTION

The present disclosure provides optically pure N-substituted-3-methoxypropionic acid compounds represented by formula (I)

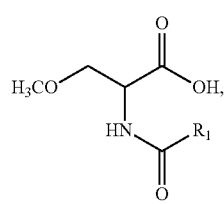

wherein $R_1$ is $C_{1-5}$ alkyl, $C_{1-6}$ alkoxy or $C_{6-10}$ aryloxy group.

The whole process for preparing optically pure N-substituted-3-methoxypropionic acid represented by formula (I) is summarized in the following scheme:

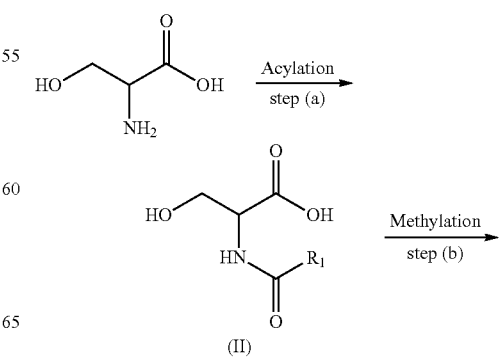

-continued

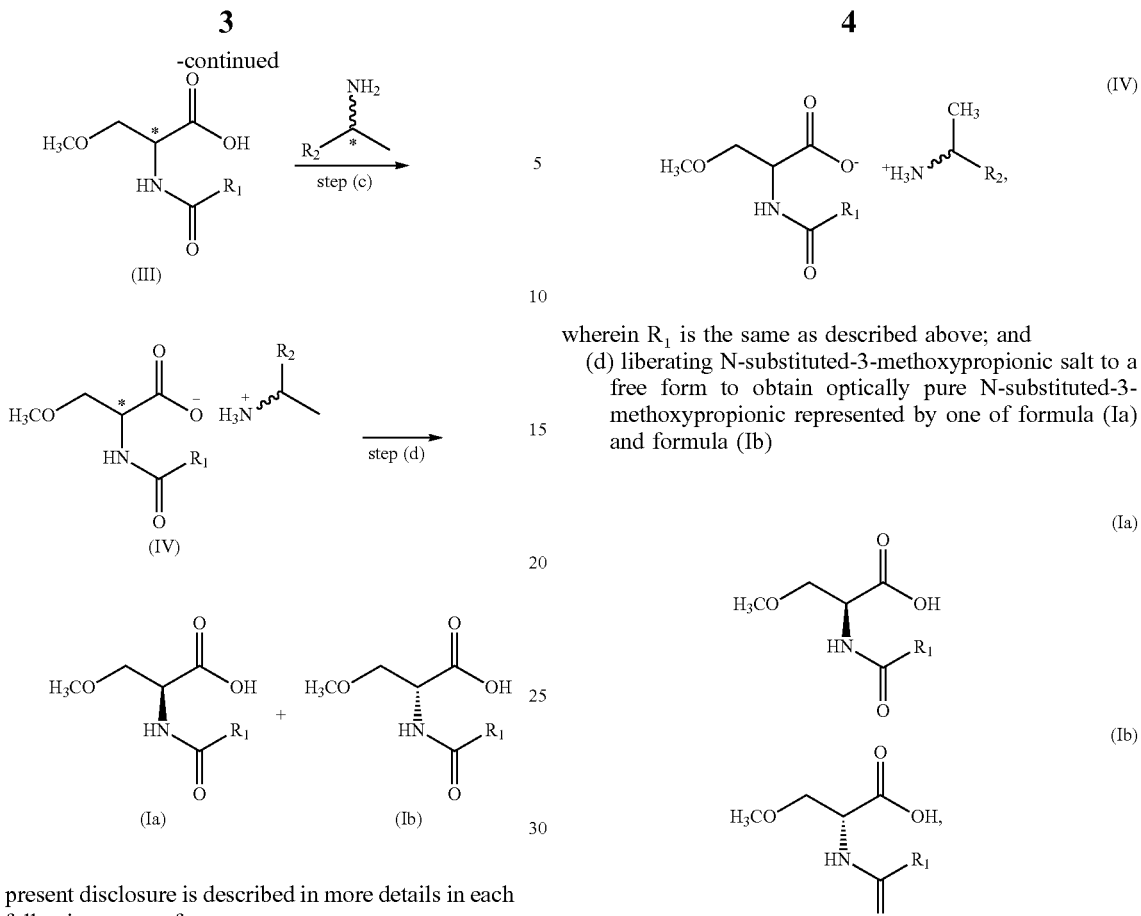

wherein $R_1$ is the same as described above; and (d) liberating N-substituted-3-methoxypropionic salt to a free form to obtain optically pure N-substituted-3-methoxypropionic represented by one of formula (Ia) and formula (Ib)

wherein $R_1$ is the same as described above.

Step (a) in this process includes a reaction of L- or D-serine with acyl anhydride or chloride under an aqueous basic condition in a protic solvent (such as alcohol and $H_2O$) to obtain a compound represented by formula (II), as above depicted. Acyl anhydride or chloride is selected from acetic anhydride, Boc anhydride and benzyloxycarbonyl chloride, and it is preferably -Boc anhydride. The aqueous base is selected from sodium hydroxide, sodium bicarbonate and potassium carbonate and it is preferably sodium hydroxide. The operating temperature ranges from 10° C. to 60° C., and preferably from 25° C. to 45° C.

The present disclosure is described in more details in each of the following steps of:

(a) N-acylating D- or L-serine to form N-acylated-serine represented by formula (II)

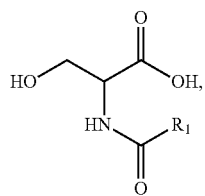

wherein $R_1$ is the same as described above;

(b) methylating N-acylated serine to form N-substituted-3-methoxypropionic represented by formula (III)

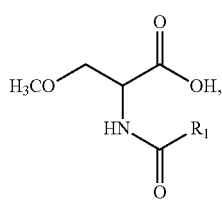

wherein $R_1$ is the same as described above;

(c) resolving N-substituted-3-methoxypropionic with a chiral amine to form a diastereomeric salt represented by formula (IV)

Step (b) in this process includes reaction of N-acylated serine represented by formula (II) with a methylating agent in the presence of an alkaline solution with or without an organic solvent or a phase transfer catalyst to obtain a compound represented by formula (III), as above depicted. The methylating agent could be dimethyl sulfate or methyl iodide, and it is preferably dimethyl sulfate. The alkaline solution could be sodium hydroxide, sodium bicarbonate, potassium hydroxide or potassium carbonate, and it is preferably sodium hydroxide. The operating temperature ranges from 0° C. to 20° C., and is preferably lower than 10° C., and is more preferably from 0° C. to 5° C.

Step (c) in this process includes a reaction of N-substituted-3-methoxy propionic acid with chiral amine to form a diastereomeric salt represented by formula (IV), as above depicted. The temperature for the formation of the diastereomeric salt ranges from 0 to 100° C., preferably from 10 to 85° C., more preferably from 25 to 85° C., yet more preferably from 70 to 85° C. The diastereomeric salt is further purified by crystallization. The solvent for crystallization is a single protic solvent (such as methanol, ethanol and isopropyl alcohol) or a mixed solvent system (such as acetone/H₂O and C$_{1-4}$ alcohol/H₂O), and it is preferably isopropyl alcohol. The crystal of the diastereomeric salt is further filtered off at a temperature lower than 30° C., preferably from 0 to 10° C. Furthermore, in the present disclosure, R$_2$ of chiral amine is C$_2$ to C$_5$ alkyl, C$_6$-C$_{18}$ cycloalkyl or C$_6$-C$_{10}$ aryl. The equivalent of chiral amine is from 0.8 to 1.5 equivalents, and is preferably 1.0 equivalent.

Step (d) in this process includes the liberation of the diastereomeric salt to a free acid in an alkaline solution. The chiral amine is washed off by an aprotic solvent, wherein the aprotic solvent is selected from ethyl ether, isopropyl ether, toluene, dichloromethane and ethyl acetate, and is preferably dichloromethane. The alkaline solution was acidified, and extracted by an aprotic solvent to provide the optically pure product represented by formula (Ia) or (Ib) with high purity and e.e. value, wherein the aprotic solvent is selected from ethyl ether, isopropyl ether, toluene, dichloromethane and ethyl acetate, and is preferably toluene.

Example 1 Synthesis of (S)-2-((tert-butoxycarbonyl)amino)-3-hydroxypropanoic acid

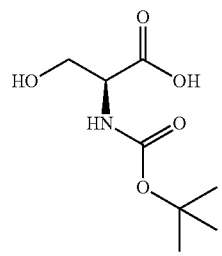

45% NaOH (123.8 kg; 1.39 kmoles) was added to a stirred solution of L-Ser (146.3 kg, 1.39 kmoles) in MeOH (224 kg) and H₂O (224 L). Boc anhydride (303.7 kg; 1.39 kmoles) was charged into reaction mixture slowly under nitrogen, and the temperature was maintained at 50° C. until no gas was released. The reaction mixture was concentrated, and used for the next step without further purification.

Example 2 Synthesis of (S)-2-((tert-butoxycarbonyl)amino)-3-methoxypropanoic acid

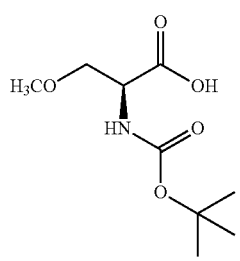

45% NaOH (746.3 kg; 8.40 kmoles) and DMS (1053.8 kg; 8.36 kmoles) were added to the reaction mixture below 10° C. over 38 h and for an additional 6 h to complete the reaction. 20% NH₄OH (20.0 kg) was added to quench the reaction in the reaction mixture. The pH value was adjusted by citric acid monohydrate (55.8 kg) and 32% HCl (180 kg) to around 3. The product was extracted by toluene (1165 L) twice, and the organic layer was washed by 1% NaOH (40 L) and H₂O (39 L×2). The organic layer was concentrated, and stripped by IPA as oil residue (240.3 kg)

Example 3 Synthesis of (S)-1-phenylethanaminium (S)-2-((tert-butoxycarbonyl)amino)-3-methoxypropanoate

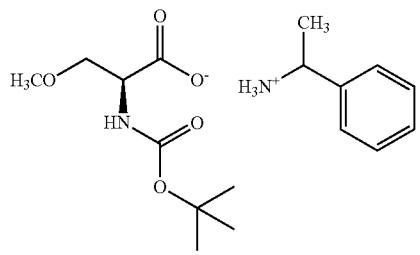

The oil residue was dissolved in IPA (1490.0 kg), and (S)-(−)-α-methyl benzylamine (132.9 kg; 1.10 kmoles) was added to the mixture at 25 to 75° C. The solution was cooled to 0 to 5° C., and filtered off. The product was washed by cool IPA (390 kg), and dried to obtain the product (352.3 kg; 94.3%). Purity was >99% by HPLC; e.e. >99.5%

Example 4 Purification of (S)-2-((tert-butoxycarbonyl)amino)-3-methoxypropanoic

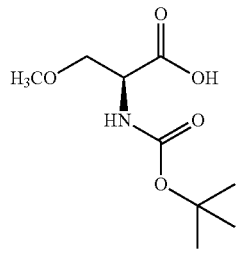

A wet cake of (S)-1-phenylethanaminium(S)-2-((tert-butoxycarbonyl)amino)-3-methoxypropanoate (305.2 g) was dissolved in H₂O (485 g), and treated with 45% NaOH (55.4 g). DCM (800 mL) was added to wash off the solution several times. The aqueous layer was acidified by citric acid (30 g) and 32% HCl (61.3 g) to around pH=3. The product was extracted by toluene (300 mL×2). The combined organic layer was washed by 0.1% NaOH (25 g) and H₂O (100 mL×2). The organic layer was concentrated at 50° C. to obtain oil residue (116.8 g). Purity was >99% by HPLC; e.e. >99.5%

The invention claimed is:
1. A method of producing optically pure N-substituted-3-methoxy propionic acid, comprising:
reacting N-substituted-3-methoxy propionic acid represented by formula (III):

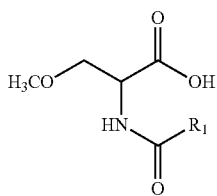
(III)

with a chiral amine in a solvent to form a diastereomeric salt represented by formula (IV):

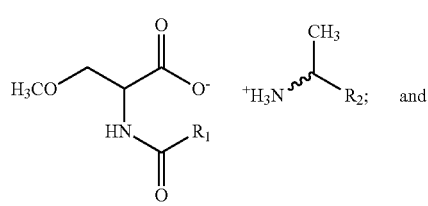
(IV)

subjecting the diastereomeric salt to a sequential washing process to obtain the optically pure N-substituted-3-methoxy propionic acid represented by one of formulae (Ia) and (Ib):

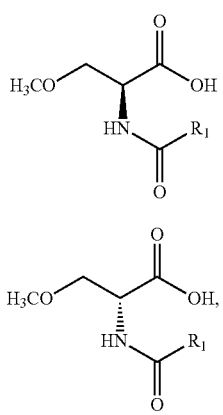
(Ia)
(Ib)

wherein $R_1$ is selected from the group consisting of $C_{1-5}$ alkyl, $C_{1-6}$ alkoxy and $C_{6-10}$ aryloxy, and $R_2$ is selected from the group consisting of $C_{2-5}$ alkyl, $C_{6-8}$ cycloalkyl and $C_{6-10}$ aryl.

2. The method according to claim 1, further comprising methylating N-substituted-3-hydroxypropionic acid represented by formula (II):

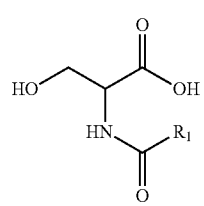
(II)

in the presence of an alkaline solution without an organic solvent or a phase transfer catalyst to obtain the N-substituted-3-methoxy propionic acid represented by formula (III).

3. The method according to claim 2, wherein the alkaline solution is selected from the group consisting of NaOH, KOH, $K_2CO_3$, and $Na_2CO_3$.

4. The method according to claim 2, wherein the methylating is performed at a temperature lower than 10° C.

5. The method according to claim 2, further comprising N-acylating D- or L-serine to obtain the N-substituted-3-hydroxypropionic acid represented by formula (II).

6. The method according to claim 1, wherein $R_1$ is tert-butyloxy or methyl.

7. The method according to claim 1, wherein $R_2$ is phenyl.

8. The method according to claim 1, wherein the cation of the diastereomeric salt is α-methylbenzylamine.

9. The method according to claim 8, wherein the α-methylbenzylamine is in an amount of from 0.8 to 1.5 equivalent.

10. The method according to claim 1, wherein the formation of the diastereomeric salt is carried out at a temperature between 25° C. and 85° C.

11. The method according to claim 10, wherein the temperature for the formation of the diastereomeric salt is in a range of from 70° C. to 85° C.

12. The method according to claim 1, further comprising filtering off a crystal of the diastereomeric salt represented by formula (IV) at a temperature lower than 30° C.

13. The method according to claim 1, wherein the temperature for filtering off the crystal of the diastereomeric salt represented by formula (IV) is in a range of from 0° C. to 10° C.

14. The method according to claim 1, wherein the solvent is a single protic solvent.

15. The method according to claim 14, wherein the single protic solvent is isopropanol.

16. The method according to claim 1, wherein the solvent is a mixed solvent system.

17. The method according to claim 16, wherein the mixed solvent system is $C_{1-4}$ alcohol/$H_2O$ or acetone/$H_2O$.

18. The method according to claim 1, wherein the chiral amine is washed off in the sequential washing process by an aprotic solvent in the presence of an alkaline solution.

19. The method according to claim 18, wherein the aprotic solvent is dichloromethane.

20. The method according to claim 1, wherein the optically pure N-substituted-3-methoxy propionic acid is represented by the following formula:

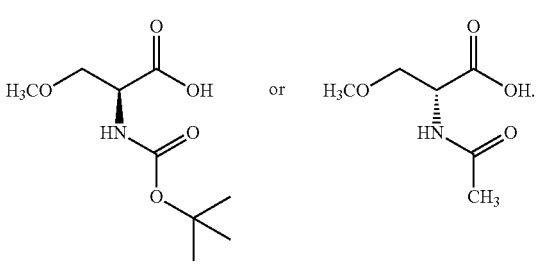

* * * * *